United States Patent [19]
Schwartz

[11] Patent Number: 5,968,960
[45] Date of Patent: Oct. 19, 1999

[54] USE OF THIAZOLIDINEDIONES TO AMELIORATE THE ADVERSE CONSEQUENCES OF MYOCARDIAL ISCHEMIA ON MYOCARDIAL FUNCTION AND METABOLISM

[75] Inventor: Gregory G. Schwartz, San Francisco, Calif.

[73] Assignee: The Regents of the University of California, Oakland, Calif.

[21] Appl. No.: 09/231,413

[22] Filed: Jan. 14, 1999

[51] Int. Cl.⁶ ................................. A61K 31/425
[52] U.S. Cl. ............................ 514/369; 514/370
[58] Field of Search ..................... 514/369, 370

[56] References Cited

U.S. PATENT DOCUMENTS 4,444,779  4/1984  Kawamatsu et al. ............ 424/263
4,572,912  2/1986  Yoshioka et al. ............... 514/369
4,703,052  10/1987  Eggler et al. .................. 514/337
5,814,647  9/1998  Urban et al. ................... 514/369

*Primary Examiner*—Raymond Henley, III
*Attorney, Agent, or Firm*—Richard Aron Osman

[57] ABSTRACT

The present invention provides methods and compositions for (a) enhancing resistance to myocardial ischemia associated dysfunction, including contraction (systolic), relaxation (diastolic) and metabolic dysfunction, comprising the step of administering to a human determined to be susceptible to myocardial ischemia an effective amount of an insulin sensitizer; and (b) reducing hypertension comprising the step of administering to a hypertensive human determined to have normal insulin sensitivity, an effective amount of an insulin sensitizer. In a particular embodiment, the sensitizer comprises a thiazolidinedione compound, such as triglitazone.

35 Claims, No Drawings

USE OF THIAZOLIDINEDIONES TO AMELIORATE THE ADVERSE CONSEQUENCES OF MYOCARDIAL ISCHEMIA ON MYOCARDIAL FUNCTION AND METABOLISM

The research carried out in the subject application was supported in part by a grant from the National Institutes of Health. The government may have rights in any patent issuing on this application.

FIELD OF THE INVENTION

The field of the invention is the use of insulin sensitizers such as thiazoladinedione compounds to reduce functional and metabolic abnormalities of the myocardium consequent to ischemia and to reduce hypertension in non-diabetic patients.

BACKGROUND OF THE INVENTION

Ischemic heart disease remains the most common cause of death in the United States. For many years, metabolic protection of the ischemic heart has been an important but elusive goal in the treatment of myocardial ischemia. Acute myocardial ischemia adversely alters both myocardial energy substrate metabolism and contractile function; in fact, these abnormalities are related, suggesting the potential importance of metabolic intervention in ischemic heart disease.

The abnormalities of myocardial substrate metabolism observed during ischemia and during reperfusion are different. During ischemia, myocardial oxygen supply is limited and anaerobic (glycolytic) metabolism becomes a relatively more important mechanism of ATP synthesis. The energy sources for anaerobic glycolysis are exogenous glucose and myocardial glycogen. In experimental models of low-flow ischemia, interventions that increase availability and myocardial uptake of exogenous glucose and/or pre-ischemic myocardial glycogen content result in greater postischemic recovery of contractile function (1,2).

During reperfusion, an adequate supply of oxygen is delivered to the myocardium, but glucose oxidation remains depressed (3). The hallmark of this abnormality is that a disproportionate fraction of myocardial glucose uptake continues to undergo anaerobic glycolysis to lactate (4). In the absence of irreversible ischemic injury, oxidation of fatty acids and oxygen consumption by reperfused myocardium usually remains normal, or even increased (5). These findings indicate preserved flux through the TCA cycle and electron transport chain. Therefore, the most likely explanation for the characteristic depression of glucose oxidation in reperfused myocardium is diminished activity of pyruvate dehydrogenase.

Fatty acids contribute to the deleterious effects of ischemia and reperfusion on the myocardium. Uptake of FFA is proportional to circulating FFA concentrations (6), which rise in acute myocardial infarction (7). Myocardial uptake of FFA and accumulation of FFA metabolites during ischemia may exert a direct, deleterious effect on mitochondrial function, ion channels, and the recovery of contractile function after reperfusion (8). Furthermore, there is a reciprocal relation between myocardial oxidation of FFA and carbohydrates: Increased utilization of FFA increases mitochondrial acetyl-CoA and NADH, both of which inhibit pyruvate dehydrogenase (9). Therefore, an intervention that reduces circulating FFA concentrations, myocardial FFA uptake and metabolism will indirectly promote oxidation of glucose. In sum, an ideal metabolic intervention would promote myocardial glucose uptake prior to and during ischemia, promote myocardial glucose oxidation during reperfusion, and reduce circulating FFA concentrations and/or myocardial FFA uptake during ischemia.

Among the pharmacologic interventions that have been employed to improve myocardial metabolism during and following acute ischemia are glucose and insulin, agents that stimulate pyruvate dehydrogenase activity (e.g., pyruvate, dichloroacetate), other agents that enhance glucose oxidation and/or reduce FFA oxidation (e.g., ranolazine, trimetazidine, L-carnitine), and inhibitors of FFA oxidation (e.g., oxfenicine, etomoxir). Several of these agents have yielded initial positive results in experimental myocardial ischemia and/or clinical studies in patients with ischemic heart disease; however, their further development and application have been limited by discordant findings in isolated heart versus in vivo models or by difficulties in administering the agent in the clinical setting.

Infusion of glucose and insulin ('GIK' when used with potassium in vivo) is the prototype metabolic intervention in myocardial ischemia. Pre-ischemic treatment with glucose and insulin increases myocardial glycogen stores, treatment during ischemia enhances anaerobic glycolytic energy generation, and treatment during reperfusion may also enhance myocardial glucose metabolism (10). GIK has been shown to limit experimental myocardial infarct size and to improve recovery of contractile function after ischemia in isolated, perfused hearts (11).

Recently, our laboratory demonstrated that GIK significantly improves recovery of both systolic and diastolic function following regional low-flow ischemia in vivo in pigs (12). GIK appeared promising in several early clinical trials (13), but its clinical application has not advanced because it cannot be applied in an anticipatory manner and requires careful monitoring to avoid excessive hyperglycemia or hypoglycemia.

Dichloroacetate and pyruvate stimulate the activity of pyruvate dehydrogenase, increase carbohydrate oxidation, and improve post-ischemic recovery of cardiac function in animal models (14). However, clinical application of these agents has been impeded by short half life and the requirement for millimolar blood concentrations to achieve optimal treatment effect (15).

Ranozaline and trimetazidine both increase myocardial glucose oxidation and reduce FFA oxidation after ischemia in isolated perfused rat hearts, and appear to limit angina and exercise-induced ECG changes in small clinical trials of patients with ischemic heart disease (16–19). These drugs appear to increase glucose oxidation and reduce FFA oxidation, perhaps through an effect on PDH. However, neither of these agents has been effective in reducing post-ischemic myocardial contractile dysfunction or infarct size in large animal in vivo models (20,21).

L-carnitine has been shown to augment myocardial glucose metabolism during and following experimental ischemia, and to attenuate left ventricular dilatation and remodeling after myocardial infarction in patients (22,23). However, this agent also has been disappointingly ineffective in attenuating contractile dysfunction after experimental low-flow ischemia in vivo (24).

Inhibitors of FFA metabolism such as oxfenicine have been shown to attenuate post-ischemic dysfunction in some in vivo studies (25) but not others (26) and have been shown to promote potentially deleterious accumulation of myocardial lipid and to cause chronic mitochondrial dysfunction (27,28).

TABLE 1

Previously Employed Metabolic Strategies in Myocardial Ischemia

| Treatment | Drawbacks for Clinical Application |
|---|---|
| GIK | IV administration |
| | Difficult to use in anticipatory fashion |
| | Careful monitoring required |
| Dichloroacetate | IV administration |
| Pyruvate | Difficult to use in anticipatory fashion |
| | Millimolar concentration required |
| Ranolazine | no convincing evidence of improved post-ischemic |
| Trimetazidine | recovery of LV function in vivo |
| L-carnitine | |
| Inhibitors of FFA metabolism | no consistent evidence of improved post-ischemic function |
| | accumulation of myocardial lipid |
| | possible chronic mitochondrial damage |

Thus, despite the interest in and potential importance of metabolic intervention in ischemic heart disease, there is currently no clearly effective and readily applicable agent for clinical use in acute myocardial ischemia.

The present invention relates to a new use for a series of known compounds, including thiazolidinedione compounds, oxazolidinedione compounds, isoxazolidinedione compounds and oxadiazolidinedione compounds, in the treatment of myocardial ischemia and reduction or prevention of myocardial ischemia associated dysfunction. We have now surprisingly discovered that the class of compounds now known as "insulin sensitizers", and which includes various thiazolidinedione compounds, oxazolidinedione compounds, isoxazolidinedione compounds and oxadiazolidinedione compounds, has the ability to reduce mechanical (systolic and diastolic) and/or metabolic dysfunction consequent to myocardial ischemia. In addition, we have found these compositions effective for enhancing insulin sensitivity to supranormal levels and reducing hypertension in hypertensive patients determined to be non-diabetic and/or have normal insulin sensitivity.

SUMMARY OF THE INVENTION

The present invention provides methods and compositions for treating myocardial ischemia and/or ameliorating adverse consequences of myocardial ischemia on myocardial function and/or metabolism by administering to a mammal, preferably a human, determined to be suffering from and/or susceptible to myocardial ischemia, an effective amount of an insulin sensitizer sufficient to reduce the myocardial ischemia and/or ameliorate the adverse consequences of myocardial ischemia. In a particular embodiment, the methods provide enhanced resistance to myocardial ischemia associated dysfunction, including contraction (systolic), relaxation (diastolic) and metabolic dysfunction, especially substrate and/or energy metabolism dysfunction of the myocardium, comprising the step of administering to a human determined to be susceptible to myocardial ischemia an effective amount of an insulin sensitizer sufficient to enhance the resistance of the human to myocardial ischemia associated dysfunction. The subject methods and compositions may also be used to increase insulin sensitivity and lower circulating free fatty acid concentrations in the blood of humans, particularly humans who are not diabetic or pre-diabetic. Preferred compositions and methods employ an effective amount of a thiazolidinedione compound, such as troglitazone. The subject compositions also find use in reducing hypertenstion. In particular, the invention also provides methods for reducing hypertension comprising the step of administering to a human determined to be hypertensive and have normal insulin sensitivity, an effective amount of an insulin sensitizer sufficient to reduce the hypertension of said human.

DETAILED DESCRIPTION OF PREFERRED EMBODIMENTS OF THE INVENTION

The following descriptions of particular embodiments and examples are offered by way of illustration and not by way of limitation.

The term insulin sensitizer, or insulin resistance-improving agent, embraces a wide variety of compounds, typically thiazolidinedione compounds, oxazolidinedione compounds, isoxazolidinedione compounds and oxadiazolidinedione compounds. One class of preferred insulin sensitizers for use in the method of the present invention are those thiazolidinedione compounds of formula (I):

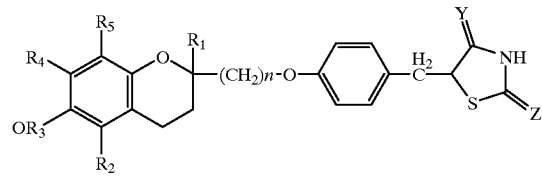

wherein:

$R^1$ and $R^2$ are the same as or different from each other and each represents a hydrogen atom or an alkyl group having from 1 to 5 carbon atoms;

$R^3$ represents a hydrogen atom, an aliphatic acyl group having from 1 to 6 carbon atoms, a cycloalkanecarbonyl group having from 5 to 7 carbon atoms in the cycloalkane part, a benzoyl group, a naphthoyl group, a benzoyl or naphthoyl group which is substituted by at least one substituent selected from the group consisting of substituents α, defined below, a heterocyclic acyl group in which the heterocyclic part has from 4 to 7 ring atoms of which from 1 to 3 are hetero-atoms selected from the group consisting of nitrogen, oxygen and sulfur atoms, a phenylacetyl group, a phenylpropionyl group, a phenylacetyl or phenylpropionyl group which is substituted by at least one halogen substituent, a cinnamoyl group, an alkoxycarbonyl group having from 1 to 6 carbon atoms in the alkoxy part or a benzyloxycarbonyl group;

$R^4$ and $R^5$ are the same as or different from each other and each represents a hydrogen atom, an alkyl group having from 1 to 5 carbon atoms or an alkoxy group having from 1 to 5 carbon atoms, or $R^4$ and $R^5$ together represent an alkylenedioxy group having from 1 to 4 carbon atoms;

n is 1,2 or 3;

Y and Z are the same as or different from each other and each represents an oxygen atom or an imino group; and substituents α are selected from the group consisting of alkyl groups having from 1 to 4 carbon atoms, alkoxy groups having from 1 to 4 carbon atoms, halogen atoms, hydroxy groups, amino groups, alkylamino groups having from 1 to 4 carbon atoms, dialkylamino groups having from 1 to 4 carbon atoms in each alkyl part, and nitro groups;

and pharmaceutically acceptable salts thereof.

In the compounds of formula (I) used in the present invention, where $R^1$ represents an alkyl group having from 1 to 5 carbon atoms, this may be a straight or branched chain alkyl group having from 1 to 5 carbon atoms, and examples include the methyl, ethyl, propyl, isopropyl, butyl, isobutyl, sec-butyl, t-butyl, pentyl and isopentyl groups, of which the methyl, ethyl, propyl, isopropyl, butyl, isobutyl and pentyl groups are preferred. Of these, those alkyl groups having from 1 to 4 carbon atoms are more preferred, and the methyl group is most preferred.

Where $R^2$ or $R^5$ represents an alkyl group having from 1 to 5 carbon atoms, this may be a straight or branched chain alkyl group having from 1 to 5 carbon atoms, and examples include the methyl, ethyl, propyl, isopropyl, butyl, isobutyl, sec-butyl, pentyl and isopentyl groups, of which the methyl, ethyl, propyl, isopropyl, butyl, isobutyl and pentyl groups are preferred. Of these, those alkyl groups having from 1 to 3 carbon atoms are more preferred, and the methyl group is most preferred.

Where $R^3$ represents an aliphatic acyl group, this may be a straight or branched chain group having from 1 to 6 carbon atoms, preferably an alkanoyl group having from 1 to 6 carbon atoms, for example a formyl, acetyl, propionyl, butyryl, isobutyryl, valeryl, isovaleryl, pivaloyl or hexanoyl group, of which the formyl, acetyl, propionyl, butyryl, isobutyryl, valeryl and hexanoyl groups are preferred. Those aliphatic acyl groups, particularly those alkanoyl groups, having from 1 to 4 carbon atoms are preferred and the acetyl group is most preferred.

Where $R^3$ represents an aromatic acyl group, this is a benzoyl or naphthoyl group in which the aromatic ring may be unsubstituted or it may be substituted by at least one substituent selected from the group consisting of substituents α, defined above and exemplified below. Examples of such substituents α include:

alkyl groups having from 1 to 4 carbon atoms, which may be straight or branched chain groups, such as the methyl, ethyl, propyl, isopropyl, butyl, isobutyl, sec-butyl and t-butyl groups, of which we prefer the methyl and t-butyl groups;

alkoxy groups having from 1 to 4 carbon atoms, which may be straight or branched chain groups, such as the methoxy, ethoxy, propoxy, isopropoxy, butoxy, isobutoxy, sec-butoxy and t-butoxy groups, of which we prefer the methoxy group;

halogen atoms, such as the fluorine, chlorine, bromine and iodine atoms, of which we prefer the fluorine and chlorine atoms;

hydroxy groups;

amino groups;

alkylamino groups having from 1 to 4 carbon atoms, which may be straight or branched chain groups, such as the methylamino, ethylamino, propylamino, isopropylamino, butylamino, isobutylamino, sec-butylamino, and t-butylamino groups, of which we prefer the methylamino group;

dialkylamino groups having from 1 to 4 carbon atoms in each alkyl part, which may be straight or branched chain groups, such as the dimethyl-amino, diethylamino, dipropylamino, diisopropylamino, dibutylamino, diisobutylamino, di-sec-butylamino, di-t-butylamino, N-methyl-N-ethylamino, N-methyl-N-propylamino, N-methyl-N-isopropylamino, N-methyl-N-butylamino, N-methyl-N-isobutylamino, N-methyl-N-sec-butylamino, N-methyl-N-t-butylamino, N-ethyl-N-propylamino, N-ethyl-N-isopropylamino, N-ethyl-N-butylamino, N-ethyl-N-isobutylamino, N-ethyl-N-sec-butylamino, N-ethyl-N-t-butylamino, N-propyl-N-isopropylamino, N-propyl-N-butylamino, N-propyl-N-isobutylamino, N-propyl-N-sec-butylamino, N-propyl-N-t-butylamino, N-isopropyl-N-butylamino, N-isopropyl-N-isobutylamino, N-isopropyl-N-sec-butylamino, N-isopropyl-N-t-butylamino, N-butyl-N-isobutyl-amino, N-butyl-N-sec-butylamino, N-butyl-N-t-butylamino, N-isobutyl-N-sec-butylamino, N-isobutyl-N-t-butylamino and N-sec-butyl-N-t-butylamino groups, of which we prefer the dimethylamino group; and nitro groups.

Where $R^3$ represents a substituted benzoyl or naphthoyl group, there is no particular restriction on the number of substituents, except such as may be imposed by the number of substitutable positions (5 in the case of benzoyl or 7 in the case of naphthoyl) and possibly by steric constraints. However, in general, we prefer from 1 to 3 substituents. Where there is more than one substituent, the substituents may be the same as or different from one another.

Examples of such substituted and unsubstituted benzoyl or naphthoyl groups include the benzoyl, 4-nitrobenzoyl, 3-fluorobenzoyl, 2-chlorobenzoyl, 3,4-dichlorobenzoyl, 4-aminobenzoyl, 3-dimethylaminobenzoyl, 2-methoxybenzoyl, 3,5-di-t-butyl-4-hydroxybenzoyl and 1- and 2-naphthoyl groups. Of these, we prefer the unsubstituted benzoyl and 1-naphthoyl groups, and most prefer the benzoyl group.

Where $R^3$ represents a cycloalkanecarbonyl group, this has from 5 to 7 carbon atoms in the cycloalkane ring, and thus a total of from 6 to 8 carbon atoms in the whole group. Examples of such groups include the cyclopentanecarbonyl, cyclohexanecarbonyl and cycloheptanecarbonyl groups, of which the cyclohexanecarbonyl group is preferred.

Where $R^3$ represents a heterocyclic acyl group, this is a group in which a heterocyclic group is attached to a carbonyl group. The heterocyclic part has from 4 to 7 ring atoms, more preferably 5 or 6 ring atoms, of which from 1 to 3, more preferably 1 or 2 and most preferably 1, are hetero-atoms selected from the group consisting of nitrogen, oxygen and sulfur atoms.

Where there are 3 hetero-atoms in the heterocyclic group, these are preferably all nitrogen atoms or one or two are nitrogen atoms and, correspondingly, two or one are oxygen and/or sulfur atoms. The heterocyclic group is preferably aromatic. Examples of preferred heterocyclic acyl groups include the furoyl (more preferably 2-furoyl), thenoyl (more preferably 3-thenoyl), 3-pyridinecarbonyl (nicotinoyl) and 4-pyridinecarbonyl (isonicotinoyl) groups.

Where $R^3$ represents a phenylacetyl or phenylpropionyl group which is substituted, preferably on the phenyl group, by at least one halogen substituent, the halogen substituent may be a fluorine, chlorine, bromine or iodine atom, and there may be from 1 to 5 such halogen substituents, preferably from 1 to 3 halogen substituents, and more preferably 1 halogen substituent. Examples of such groups include the p-chlorophenylacetyl, p-fluorophenylacetyl, p-bromophenylacetyl, p-iodophenylacetyl, o-chlorophenylacetyl, o-fluorophenylacetyl, o-bromophenyl-acetyl, o-iodophenylacetyl, m-chlorophenylacetyl, m-fluorophenylacetyl, m-bromophenylacetyl, m-iodophenylacetyl, 2,4-dichlorophenylacetyl, 2,4-difluorophenylacetyl, 2,4-dibromophenylacetyl, 2,4-diiodophenylacetyl, 3-(p-chlorophenyl)propionyl, 3-(p-fluorophenyl)propionyl, 3-(p-bromophenyl)-propionyl, 3-(p-iodophenyl) propionyl, 3-(o-chlorophenyl)propionyl, 3-(o-fluoro-phenyl)propionyl, 3-(o-bromophenyl)propionyl, 3-(o-iodophenyl)propionyl, 3-(m-chlorophenyl)propionyl, 3-(m-fluorophenyl) propionyl, 3-(m-bromophenyl)-propionyl, 3-(m-iodophenyl)propionyl, 3-(2,4-dichlorophenyl)propionyl, 3-(2,4-difluorophenyl)propionyl, 3-(2,4-dibromophenyl) propionyl and 3-(2,4-diiodo-phenyl)propionyl groups, of which the p-chlorophenylacetyl group is most preferred.

Where $R^3$ represents an alkoxycarbonyl group, this may be a straight or branched chain alkoxycarbonyl group having from 1 to 6 carbon atoms in the alkoxy part, i.e. having a total of from 2 to 7 carbon atoms, such as the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl and hexyloxycarbonyl groups, of which we prefer those alkoxycarbonyl group having from 2 to 4 carbon atoms and most prefer the ethoxycarbonyl group.

Where $R^4$ represents an alkyl group, this may be a straight or branched chain alkyl group having from 1 to 5 carbon atoms, such as the methyl, ethyl, propyl, isopropyl, butyl, isobutyl, t-butyl and pentyl groups, of which we prefer those alkyl groups having from 1 to 4 carbon atoms, more preferably a methyl or t-butyl group, and most preferably a methyl group.

Where $R^4$ or $R^5$ represents an alkoxy group, this may be a straight or branched chain alkoxy group having from 1 to 5 carbon atoms, such as the methoxy, ethoxy, propoxy, isopropoxy, butoxy, isobutoxy, t-butoxy and pentyloxy groups, of which we prefer those alkoxy groups having from 1 to 4 carbon atoms, more preferably a methoxy or t-butoxy group, and most preferably a methoxy group.

Where $R^4$ and $R^5$ together represent an alkylenedioxy group, this has from 1 to 4 carbon atoms and examples include the methylenedioxy, ethylenedioxy, propylenedioxy, trimethylenedioxy and tetramethylenedioxy groups, of which the methylenedioxy and ethylenedioxy groups are preferred.

n is 1,2 or 3, but is preferably 1.

Y and Z are the same as or different from each other and each represents an oxygen atom or an imino group; however, both are preferably oxygen atoms.

Preferred compounds used in the present invention are those compounds of formula (Ia):

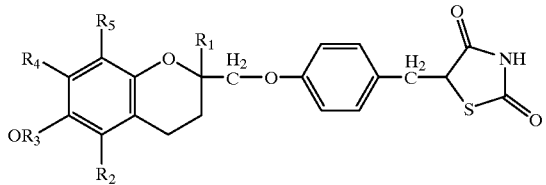

wherein:
$R^1$, $R^2$, $R^4$ and $R^5$ are the same as or different from each other and each represents a hydrogen atom or an alkyl group having from 1 to 5 carbon atoms; and $R^3$ represents a hydrogen atom, an aliphatic acyl group having from 1 to 6 carbon atoms, a benzoyl group, a naphthoyl group, a benzoyl or naphthoyl group which is substituted by at least one substituent selected from the group consisting of substituents α, defined below, or an alkoxycarbonyl group having from 1 to 6 carbon atoms in the alkoxy part;

substituents α are selected from the group consisting of alkyl groups having from 1 to 4 carbon atoms, alkoxy groups having from 1 to 4 carbon atoms, halogen atoms, hydroxy groups, amino groups, alkylamino groups having from 1 to 4 carbon atoms, dialkylamino groups having from 1 to 4 carbon atoms in each alkyl part, and nitro groups;

and pharmaceutically acceptable salts thereof.

Preferred classes of compounds used in the present invention are those compounds of formula (I) or (Ia) and pharmaceutically acceptable salts thereof, in which:

(A) $R^1$ represents an alkyl group having from 1 to 4 carbon atoms.

(B) $R^2$ represents a hydrogen atom or an alkyl group having from 1 to 3 carbon atoms.

(C) $R^3$ represents a hydrogen atom, an aliphatic acyl group having from 1 to 4 carbon atoms, an unsubstituted benzoyl or naphthoyl group, or an alkoxycarbonyl group having from 2 to 4 carbon atoms.

(D) $R^4$ represents an alkyl group having from 1 to 4 carbon atoms.

(E) $R^5$ represents a hydrogen atom or an alkyl group having from 1 to 3 carbon atoms.

In particular, of the above compounds, we prefer those compounds of formula (I) and (Ia), in which $R^1$ is as defined in (A) above, $R^2$ is as defined in (B) above, $R^3$ is as defined in (C) above, $R^4$ is as defined in (D) above, and $R^5$ is as defined in (E) above.

More preferred classes of compounds used in the present invention are those compounds of formula (I) and (Ia) and pharmaceutically acceptable salts thereof, in which:

(F) $R^1$ represents an alkyl group having from 1 to 4 carbon atoms.

(G) $R^2$ represents a hydrogen atom or an alkyl group having from 1 to 3 carbon atoms.

(H) $R^3$ represents a hydrogen atom, an acetyl group, a benzoyl group or an ethoxycarbonyl group.

(I) $R^4$ represents an alkyl group having from 1 to 4 carbon atoms.

(J) $R^5$ represents a hydrogen atom or an alkyl group having from 1 to 3 carbon atoms.

In particular, of the above compounds, we prefer those compounds of formula (I) and (Ia), in which $R^1$ is as defined in (F) above, $R^2$ is as defined in (G) above, $R^3$ is as defined in (H) above, $R^4$ is as defined in (I) above, and $R^5$ is as defined in (J) above.

The most preferred classes of compounds used in the present invention are those compounds of formula (I) and (Ia) and pharmaceutically acceptable salts thereof, in which:

(K) $R^1$ represents a methyl group.

(L) $R^2$ represents a hydrogen atom or a methyl group.

(M) $R^3$ represents a hydrogen atom, an acetyl group or an ethoxycarbonyl group.

(N) $R^4$ represents a methyl or a t-butyl group.

(O) $R^5$ represents a hydrogen atom or a methyl group.

In particular, of the above compounds, we prefer those compounds of formula (I) and (Ia), in which $R^1$ is as defined in (K) above, $R^2$ is as defined in (L) above, $R^3$ is as defined in (M) above, $R^4$ is as defined in (N) above, and $R^5$ is as defined in (O) above.

When the compounds of formula (I) of the present invention contain at least one basic group in their molecules, they can thus form acid addition salts. Examples of such acid addition salts include: salts with mineral acids, especially hydrohalic acids (such as hydrofluoric acid, hydrobromic acid, hydroiodic acid or hydrochloric acid), nitric acid, perchloric acid, carbonic acid, sulfuric acid or phosphoric acid; salts with lower alkanesulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid, benzoic acid, mandelic acid, ascorbic acid, lactic acid, gluconic acid or citric acid; and salts with amino acids, such as glutamic acid or aspartic acid. Such acid addition salts may readily be prepared by conventional means.

The compounds of the present invention can also form salts with cations, e.g. metals. Examples of such salts include: salts with an alkali metal, such as sodium, potassium or lithium; salts with an alkaline earth metal, such as barium or calcium; salts with another metal, such as magnesium or aluminum; ammonium salts; organic base salts, such as a salt with methylamine, dimethylamine, triethylamine, diisopropylamine, cyclohexylamine or dicyclohexylamine; and salts with a basic amino acid, such as lysine or arginine. Such salts may likewise readily be prepared by conventional means.

The compounds of the present invention can exist in the form of various isomers.

Thus, the carbon atom at position 2 of the chromane ring and that at position 5 of the thiazolidine ring are both asymmetric carbon atoms. In each of the compounds of formula (I) and (Ia), stereoisomers due to these asymmetric carbon atoms as well as equimolar and non-equimolar mixtures thereof are all represented by only the one formula. Accordingly, the scope of the present invention covers all of these isomers separately, as well as all mixtures thereof.

In the compounds of formula (I) in which Y and Z both represent imino groups, in which Y and Z both represent oxygen atoms and in which one of Y and Z represents an oxygen atom and the other represents an imino group can exist in the form of various tautomers as explained in Japanese Patent Kokai Application Sho 60-51189, U.S. Pat. No. 4,572,912 and European Patent No. 139 421.

In each of the compounds of formula (I) and (Ia), the tautomers and equimolar and non-equimolar mixtures thereof are all represented by only the one formula. Accordingly, the scope of the present invention covers all of these tautomers and all mixtures thereof.

The compounds of the present invention can also form solvates (for example hydrates), and the present invention embraces all such solvates.

The present invention covers additionally all of the so-called "pro-drugs" which can be converted by metabolic change in vivo into any one of the compounds of formula (I) or salts thereof.

Specific examples of the compounds of formula (I) are those compounds of formula (Ia) supra, in which $R^1$, $R^2$, $R^3$, $R^4$ and $R^5$ are as defined in the following Table 2. In the Table, the following abbreviations are used: Ac: acetyl, iBu: isobutyl, tBu: t-butyl, Byr: butyryl, Bz: benzoyl, Etc: ethoxycarbonyl, Et: ethyl, Me: methyl, Pn: pentyl

TABLE 2

| Compound No. | $R^1$ | $R^2$ | $R^3$ | $R^4$ | $R^5$ |
| --- | --- | --- | --- | --- | --- |
| 1 | Me | Me | H | Me | Me |
| 2 | H | Me | H | Me | Me |
| 3 | Me | H | H | H | H |
| 4 | Me | H | H | tBu | H |
| 5 | Et | Me | H | Me | Me |
| 6 | iBu | Me | H | Me | Me |
| 7 | Pn | Me | H | Me | Me |

TABLE 2-continued

| Compound No. | $R^1$ | $R^2$ | $R^3$ | $R^4$ | $R^5$ |
| --- | --- | --- | --- | --- | --- |
| 8 | Me | Me | Ac | Me | Me |
| 9 | Me | Me | Bz | Me | Me |
| 10 | Me | Me | Etc | Me | Me |
| 11 | Me | H | Ac | Me | H |
| 12 | Me | H | H | Me | H |
| 13 | Me | Me | Byr | Me | Me |

Of the compounds listed above, preferred compounds are Compounds No.:
1. 5-[4-(6-Hydroxy-2,5,7,8-tetramethylchroman-2-ylmethoxy)benzyl]thiazolidine-2,4-dione;
4. 5-[4-(6-Hydroxy-2-methyl-7-t-butylchroman-2-ylmethoxy)benzyl]thiazolidine-2,4-dione;
5. 5-[4-(6-Hydroxy-2-ethyl-5,7,8-trimethylchroman-2-ylmethoxy)benzyl]-thiazolidine-2,4-dione;
6. 5-[4-(6-Hydroxy-2-isobutyl-5,7,8-trimethylchroman-2-ylmethoxy)benzyl]-thiazolidine-2,4-dione;
8. 5-[4-(6-Acetoxy-2,5,7,8-tetramethylchroman-2-ylmethoxy)benzyl]thiazolidine-2,4-dione;
10. 5-[4-(6-Ethoxycarbonyloxy-2,5,7,8-tetramethylchroman-2-ylmethoxy)benzyl]-thiazolidine-2,4-dione;

and pharmaceutically acceptable salts thereof

More preferred compounds are Compounds No. 1, 4 and 10, and the most preferred compound is Compound No. 1 (commonly known as "troglitazone", by which name it is referred to hereafter).

The compounds of formula (I) and salts thereof of the present invention are known compounds, and are described in, for example, Japanese Patent Kokai Application Sho 60-51189, U.S. Pat. No. 4,572,912 and European Patent No. 0 139 421. They may be prepared as described in these documents or by other known methods.

In addition to the thiazolidine derivatives of formula (I) described above, we have found that other known insulin sensitizers can also be used for the treatment or prevention of myocardial ischemia.

Examples of such other compounds include:

i. MCC-555: 5-[6-(2-Fluorobenzyloxy)-2-naphthyhnethyl] thiazolidine-2,4-dione, which is disclosed as an antilipemic and anti-diabetic agent in Diabetes, 45, Suppl. 2, 141A (1996) and Example 4 of EP 604 983A;

ii. Pioglitazone: 5-{4-[2-(5-Ethylpyridin-2-yl)ethoxy]benzyl }thiazolidine-2,4-dione, which is disclosed as an insulin sensitizer in Japanese Patent Publication No. Sho 62-42903 and No. Hei 5-66956 and in U.S. Pat. Nos. 4,287,200, 4,340,605, 4,438,141, 4,444,779 and 4,725,610;

iii. Englitazone: 5-(2-Benzyl-3,4-dihydro-2H-benzopyran-6-ylmethyl)-thiazolidine-2,4-dione, which is disclosed as an insulin sensitizer in Japanese Patent Publication No. Hei 5-86953 and in U.S. Pat. No. 4,703,052;

iv. BRL-49653: 5-[4-{2-[N-Methyl-N-(pyridin-2-yl)amino]ethoxy}benzyl]-thiazolidine-2,4-dione, which is disclosed as an insulin sensitizer in Japanese Patent Kokai Application No. Hei 1-131169 and in U.S. Pat. Nos. 5,002,953, 5,194,443, 5,232,925 and 5,260,445;

v. Compound A: 5-(4-{2-[1-(4-2'-pyridylphenyl)ethylideneaminooxy]ethoxy}-benzyl)thiazolidine-2,4-dione, which is disclosed as an insulin sensitizer in European Patent No. 708 098A;

vi. Compound B: 4-{4-[2-(5-Methyl-2-phenyloxazol-4-yl)ethoxy]benzyl}-isoxazolidine-3,5-dione, which is disclosed as an antilipemic and anti-diabetic agent in WO 95/18125;

vii. Compound C: 5-{4-(5-Methoxy-3-methylimidazo[4,5-b]pyridin-2-yl-methoxy)benzyl}thiazolidine-2,4-dione (and its hydrochloride), which are disclosed as insulin sensitizers in Japanese Patent Kokai Application No. Hei 7-330728 and in European Patent No. 676 398A;

viii. 5-[4-(6-Methoxy-1-methylbenzimidazol-2-ylmethoxy)benzyl]thiazolidine-2,4-dione, which is disclosed as an insulin sensitizer in European Patent No. 745 600A;

ix. 5-[4-(1-Methylbenzimidazol-2-ylnethoxy)benzyl] thiazolidine-2,4-dione, which is disclosed as an insulin sensitizer in European Patent No. 745 600A;

x. 5-[4-(5-Hydroxy-1,4,6,7-tetramethylbenzimidazol-2-ylmethoxy)benzyl]-thiazolidine-2,4-dione, which is disclosed as an insulin sensitizer in European Patent No. 745 600A;

xi. 5-[4-(1-Methylindolin-2-ylmethoxy)benzyl] thiazolidine-2,4-dione, which is disclosed as an insulin sensitizer in Japanese Patent Kokai Application No. Hei 7-330728 and in European Patent No. 676 398A;

xii. Darglitazone: 5-{4-[3-(5-methyl-2-phenyloxazol-4-yl)propionyl]benzyl}-thiazolidine-2,4-dione, which is disclosed as a hypoglycemic and hypocholesterolemic agent in Japanese Patent Kokai Application No. Hei 1-272574 and in European Patent No. 332 332A.

Insulin sensitizers of the thiazolidinedione class suitable in the present invention are also described in U.S. Pat. Nos. 5,753,681; 5,824,694; 5,798,375; 5,804,590 and 5,814,647, The compounds employed in the present invention can be administered by various routes. The route of administration is not particularly critical to the present invention, and is determined according to the form of the drug preparation, and the age, sex and condition of the patient, as well as the nature and degree of the disease. For example, for oral administration, the compounds may be administered in the form of tablets, pills, powders, granules, syrups, liquid preparations, suspensions, emulsions or capsules. Injections may be given intravenously by themselves or in admixture with the usual fluid replacements, such as glucose and amino acids; or they may, if necessary, be administered intramuscularly, intracutaneously, subcutaneously or intraperitoneally by themselves. When suppositories are used, these may be administered intrarectally.

The compounds of the present invention may be administered alone or in admixture with any known additives commonly used in the field of drug preparation such as vehicles, binders, disintegrators, lubricants, solubilizers, corrigents and coating agents. Such preparations may be obtained by known means.

When tablets are to be prepared, carriers which are widely known in this field can be employed, for example: vehicles, such as lactose, sucrose, sodium chloride, glucose, urea, starch, calcium carbonate, kaolin, crystalline cellulose and silicic acid; binders, such as water, ethanol, propanol, simple syrup, glucose solution, starch solution, gelatin solution, carboxymethyl cellulose, purified shellac, methyl cellulose, potassium phosphate and polyvinylpyrrolidone; disintegrators, such as dry starch, sodium alginate, agar powder, laminaran powder, sodium bicarbonate, calcium carbonate, polyoxyethylene sorbitan fatty acid esters, sodium laurylsulfate, stearic acid monoglyceride, starch and lactose; disintegration inhibitors, such as sucrose, stearine, cacao oil and hydrogenated oil; absorption accelerators, such as quaternary ammonium bases and sodium laurylsulfate; humectants, such as glycerin and starch; adsorbers, such as starch, lactose, kaolin, bentonite and colloidal silicic acid; and lubricants, such as purified talc, salts of stearic acid, powdery boric acid and polyethylene glycol. In addition, the tablets can, if necessary, be prepared as ordinary coated tablets, such as sugar-coated tablets, gelatin-coated tablets, enteric coated tablets, film-coated tablets, or as double-layer tablets or multi-layer tablets.

When pills are to be prepared, carriers which are widely known in this field can be employed, for example: vehicles, such as glucose, lactose, starch, cacao oil, hardened vegetable oil, kaolin and talc; binders, such as gum arabic, tragacanth powder, gelatin and ethanol; and disintegrators, such as laminaran agar.

When suppositories are to be prepared, carriers which are widely known in this field can be employed, for example: polyethylene glycol, cacao oil, higher alcohols, higher alcohol esters, gelatin and semi-synthetic glycerides.

When injections are to be prepared, they may be solutions, emulsions or suspensions which are preferably sterilised and isotonic to blood. When these solutions, emulsions and suspensions are to be prepared, diluents conventionally used in this field can be employed; for example, water, ethyl alcohol, propylene glycol, ethoxy-isostearyl alcohol, polyoxy-isostearyl alcohol and fatty acid esters of polyoxyethylene sorbitan. In this case, sufficient sodium chloride, glucose or glycerin to make the solution isotonic may be included in these preparations; or ordinary solubilizers, buffers or pain suppressers may be added.

In addition, coloring agents, preservatives, perfumes, flavors, sweetening agents and any other drugs may be added, if necessary.

The amount of the active ingredient contained in these preparations is not particularly critical, and may be selected over a wide range. In general, from 1 to 70% by weight, preferably from 1 to 30% by weight, of the active ingredient may be present in the whole composition.

Although the dosage may vary depending on the symptoms, age and body weight of the patient, as well as the route of administration and the form of the drug, an upper limit of 5,000 mg (preferably 1,000 mg, and more preferably 500 mg), and a lower limit of 0.5 mg (preferably 10 mg, and more preferably 50 mg), may preferably be given daily to an adult human patient.

In a particular embodiment, the subject therapies are administered to a human determined to be susceptible to myocardial ischemia, providing enhanced resistance to myocardial ischemia associated dysfunction. Such a human has been specifically identified to be at relatively high risk of myocardial ischemic events and/or at relatively high risk for enhanced myocardial ischemia associated dysfunction. Preferably, such human has been specifically prescribed the subject therapeutics for the purpose of reducing myocardial ischemia associated dysfunction. In a particular embodiment, the methods involve pre-, pending- and/or post administrations step of diagnosis the patient, prescribing the subject therapies and/or monitoring their effectiveness and/or continued necessity of the therapy in terms of reducing myocardial ischemia associated dysfunction. Routine methods and criteria for screening compositions for effectiveness in providing resistance to myocardial ischemia associated dysfunction in humans and animal models are provided herein, in the cited literature and/or are otherwise well-known in the art, see e.g. Roman JA et al., Heart 1998 October;80(4):370–6; Hoffmann R, et al., Am J Cardiol. Dec. 15, 1998;82(12):1520–4; Brochet E, et al., J Am Coll Cardiol. 1998 December;32(7):2011–7; Ramani K, et al., Circulation. Dec. 15, 1998; 98(24):2687–94; Baumgartner H, et al., J Am Coll Cardiol. Nov. 15, 1998;32(6):1701–8; and Galati A, et al., Int J Card Imaging. 1998 June;14(3): 155–62.

In another embodiment, the subject therapies are administered to a human determined to (a) be hypertensive and (b) have normal insulin sensitivity, in an amount sufficient to reduce the hypertension of said human. In fact, all the disclosed compositions found effective at enhancing resistance to myocardial ischemia were found similarly effective in this application. Nomal baseline insulin (pretreatment) insulin sensitivity is readily determined by nomal fasting plasma insulin levels and/or normal insulin release in a standard glucose tolerance test. In addition, normal insulin sensitivity can generally be inferred from the absence of type II diabetes and metabolic syndrom X. Preferably, the hypertensive human has been further specifically prescribed the subject therapeutics for the purpose of reducing hypertension. Routine methods and criteria for screening compositions for effectiveness in providing reduced hypertension in humans and animal models are provided herein, in the cited literature and/or are otherwise well-known in the art.

The invention is further illustrated by the following examples.

EXAMPLES

Example 1

Thiazolidinediones Improve Recovery of Mechanical and Metabolic Myocardial Function after Ischemia in Model System In prior studies, the principal systemic effect of thiazolidinedione drugs was to increase insulin-mediated glucose disposal without an increase in insulin release (29), implying increased insulin sensitivity of target tissues. However, troglitazone exerts a variety of other effects. Diabetic patients and animals treated with troglitazone demonstrate a reduction in circulating FFA concentrations (30,31). Troglitazone exerts antioxidant/free radical scavenging effects (32). Other free radical scavengers have been shown to improve the recovery of myocardial function after ischemia and reperfusion (33). Troglitazone exerts inhibitory effects on L-type calcium channels in vascular smooth muscle (34). If a similar effect is exerted on myocardial L-type calcium channels during ischemia and reperfusion, myocardial calcium overload may be attenuated, affording protection from ischemic and reperfusion injury similar to that provided by other calcium channel antagonists (35).

Very few data exist regarding myocardial effects of thiazolidinediones. Bahr et al. (36), studying cultured cardiomyocytes from normal (non-diabetic) rats, showed that troglitazone (5–50 $\mu$M) increased GLUT1 and GLUT4 levels and glucose uptake (measured by accumulation of the tracer 2-deoxyglucose). Martin et al. (37) showed that the thiazolidinedione BRL 49653 increased fatty acid transport protein levels in adipose tissue but reduced the levels in myocardium, an effect that might be predicted to promote FFA uptake into adipose tissue and diminish myocardial FFA uptake. Shimabukuro et al. (38) studied normal and streptozotocin-induced diabetic rats, either with or without troglitazone treatment. Hearts from all four groups of rats were then isolated, perfused, and subjected to global ischemia followed by reperfusion. Of the four groups, the poorest recovery of LV function was observed in hearts from untreated diabetic rats. Troglitazone treatment significantly improved functional recovery of hearts from diabetic rats, to a level not different from that of hearts from non-diabetic rats, while hearts from non-diabetic rats demonstrated no benefit of troglitazone treatment. We hypothesized that there may be several potential mechanisms by which thiazolidinedione treatment could influence the recovery of myocardial function after ischemia and reperfusion, both related and unrelated to the drug's effects on myocardial glucose metabolism. However, prior to the data presented here, there was no information regarding effects of troglitazone on myocardial metabolism or on myocardial function in response to ischemia or reperfusion in vivo.

We performed experiments to determine if treatment with various insulin sensitizers improves recovery of myocardial systolic and diastolic left ventricular function following a period of low-flow ischemia. Furthermore, we examined the pattern of myocardial substrate uptake to determine if a beneficial effect of sensitizer treatment may be related to altered myocardial glucose and lactate utilization in reperfused myocardium.

Juvenile non-diabetic farm pigs (9±1 kg) were treated with compounds 1–12 of Table 2 at 75 mg/kg/day po for 8 weeks. Untreated non-diabetic pigs served as controls. Both groups of pigs weighed 31±1 kg at the time of an acute ischemic protocol: The pigs were anesthetized, the chest opened, and the heart instrumented for measurements of regional myocardial contractile function (implanted ultrasonic crystals) and myocardial metabolism (oxygen consumption; glucose, lactate, and free fatty acid uptake). Pigs were subjected to 90 min of low flow myocardial ischemia (partial constriction of the anterior descending coronary artery) and 90 min of reperfusion. The primary measures of treatment efficacy were the extent of recovery of regional systolic and diastolic function in the ischemic zone and of global left ventricular systolic and diastolic function. Detailed methods are provided in Example 2.

Chronic therapy with Compounds 1–12 resulted in statistically and physiologically significant improvement in the recovery of regional and global systolic and diastolic myocardial function after ischemia and reperfusion: for example, regional external work of the ischemic region of the heart recovered to a mean of 43% of baseline in the Compound 1 (troglitazone)-treated pigs, but to a mean of only 18% of baseline in the untreated pigs ($p<0.05$). Global left ventricular systolic function (assessed by maximum positive LV dp/dt) recovered to a mean of 78% of baseline in troglitazone-treated pigs versus a mean of 62% baseline in untreated pigs, $p<0.01$). Regional diastolic function (assessed by sonomicrometry as the maximum rate of diastolic wall area expansion) recovered to a mean of 78% of baseline in treated versus 52% of baseline in untreated pigs ($p<0.05$). Global diastolic function (assessed by maximum negative LV dp/dt) recovered to a mean of 81% of baseline in treated versus 61% of baseline in untreated pigs ($p<0.01$). Myocardial substrate uptake during reperfusion was notable for significantly greater lactate uptake in treated pigs, without intergroup differences in glucose uptake or myocardial oxygen consumption. These findings demonstrate greater myocardial oxidation of carbohydrates (glucose and lactate) in the treated groups. There was a significant reduction of circulating free fatty acid levels in treated pigs, and a trend to lower myocardial free fatty acid uptake.

In sum, chronic thiazolidinedione treatment improves the recovery of systolic and diastolic myocardial function after myocardial ischemia and reperfusion in normal (non-diabetic) pigs in vivo. Thiazolidinedione treatment increases myocardial lactate uptake after ischemia and reperfusion, without affecting myocardial glucose uptake or oxygen consumption. These findings indicate that thiazolidinedione treatment enhances myocardial glucose and/or lactate oxidation in reperfused myocardium, and may be one of the mechanisms of improved functional recovery from ischemia. Chronic thiazolidinedione treatment enhanced insulin sensitivity as indicated by decreases in circulating insulin and free fatty acid levels in normal pigs, without effect on blood glucose concentration. Our finding that thiazolidinedione treatment can increase insulin sensitivity (enable maintenance of normal blood glucose levels with reduced levels of insulin) and lower plasma free fatty acid levels in normal (non-diabetic, non-obese) animals is of particular significance. Troglitazone and other thiazolidinediones have been shown to normalize reduced insulin sensitivity and lower circulating free fatty acids in diabetic patients. However, this is the first suggestion and demonstration of reduced insulin and free fatty acid levels in normal animals. We demonstrate that troglitazone treatment can cause supranormal insulin sensitivity. As insulin resistance is associated with hypertension and insulin action causes vasodilation, enhancement of insulin sensitivity to supranormal levels provides another utility in the treatment of disorders such as hypertension.

Example 2

Non-Human Animal Model of Myocardial Ischemia: Experimental Protocols

Instrumentation of the heart: Pigs were anesthetized with α-chloralose, mechanically ventilated, and the heart exposed via median sternotomy. A solid state micromanometer was inserted in the left ventricle (LV) through a carotid artery. A fluid-filled catheter was inserted in the left atrium through its appendage for injection of microspheres used to measure regional myocardial blood flow. An adjustable hydraulic occluder and ultrasonic flow probe were placed around the anterior descending coronary artery distal to the first diagonal branch to produce and monitor graded myocardial ischemia of the anterior LV. A catheter was inserted in the anterior interventricular vein to sample coronary venous blood from the ischemic region. Two orthogonal pairs of ultrasonic crystals were implanted ~1 cm apart in the subendocardium of both the anterior and posterior LV to measure regional myocardial wall area (the instantaneous product of the two orthogonal segment lengths in each region). Hydraulic occluders were placed around the vena cavae; brief inflation of these occluders produces dynamic reduction in preload. LV pressure versus wall area loops for both regions were monitored on-line and selected segments of data digitized and stored for subsequent analysis on a Macintosh computer running customized software. Recordings of LV pressure versus wall area loops during brief occlusion of the vena cavae provided the data required to derive regional diastolic and systolic function relations (see data analysis, below).

Regional myocardial bloodflow: The fluorescent microsphere technique was employed to measure regional transmural myocardial blood flow. This technique has been described in our previous publications (39). In brief, 15 μm diameter latex microspheres labeled with a fluorescent dye are injected over 30 s into the left atrium while a reference blood sample is withdrawn from a carotid artery using a calibrated pump. Microspheres lodge in the capillary beds of all tissues in direct proportion to blood flow. Similarly, the number of microspheres in the reference blood sample is proportional to the known withdrawal rate of the pump. Up to five separate injections, each with microspheres labeled with a different dye, allow measurement of blood flow up to five times in a single experiment. At the conclusion of the experiment, 1–2 g samples of myocardium from subendocardium, mid-myocardium, and subepicardium in each region are digested, releasing the microspheres. Microspheres are also extracted from the reference blood samples. Dyes are eluted from the microspheres with a solvent, and the elutate is analyzed for fluorescence intensity using the excitation and emission wavelengths of each dye. The ratio of fluorescence from tissue specimen/reference blood sample is equal to the ratio of tissue blood flow/withdrawal rate of the pump.

Regional oxygen consumption and substrate uptake: Paired blood samples are drawn simultaneously from the aorta (via carotid artery catheter) and from the anterior interventricular coronary vein and immediately iced. Blood oxygen content and concentrations of glucose, lactate, and FFA are measured as described in our previous publications (40). Myocardial oxygen consumption and substrate uptake in the anterior LV are calculated as the product of the arteriovenous concentration difference and the mean transmural myocardial blood flow in the anterior LV as measured by the microsphere technique.

Assessment of regional and global systolic and diastolic LV function: LV pressure versus wall area loops are recorded during brief occlusion of the vena cavae. The area of each loop is a measure of regional external work. A plot of successive loop areas during vena caval occlusion versus the corresponding end-diastolic wall area for each loop provides a regional Frank-Starling, or preload-recruitable stroke work relation. This is a load-independent measure of regional systolic function. Global LV systolic function is assessed by peak positive LV dp/dt (LV+dP/dt$_{max}$).

To assess regional diastolic function, the first derivative of wall area versus time (dA/dt) is calculated. The maximum positive dA/dt (+dA/dt$_{max}$) is an indicator of the peak rate of regional diastolic wall expansion, equivalent to a global LV peak filling rate. Global LV diastolic function is assessed by LVEDP and by peak negative LV dp/dt (LV−dp/dt$_{max}$).

Acute ischemic protocol: Baseline measurements of hemodynamics, regional LV function, myocardial blood flow and substrate uptake, and plasma insulin were obtained. The left anterior descending coronary artery was then partially constricted to reduce total LAD flow by 50%; this level of flow restriction was then maintained for 90 min. A second complete set of measurements was made during the final 15 min of the ischemic period. After 90 min of ischemia, the LAD constriction was released. The third complete set of measurements was made during the final 15 min of the 90 min reperfusion period.

Example 3

Protocol for Determining the Effect of Thiazolidinedione Treatment on Stress

Test Induced Ischemic Myocardial Dysfunction in Humans.

The efficacy of candidate insulin sensitizers in the disclosed methods is readily demonstrated clinically by routine stress testing. For example, the efficacy of Compounds 1–12 in providing enhanced resistance to myocardial ischemia associated dysfunction in humans is demonstrated as follows (see, Lu et al., Amer.J.Cardiol., Oct. 1, 1998, 82, 898–901). Following run-in dobutamine echocardiographic testing (DET), patients are blindly and randomly assigned to a placebo or insulin sensitizer treatment (e.g. thiazolidinedione) group. Resting electrocardiography and 2-dimensional echocardiography are performed with the patient lying in the left lateral recumbent position. Images are obtained from the standard parastemal long-and short axis views as well as the apical long-axis, and apical 4- and 2-chamber views. Dobutamine is infused with a mechanical pump, starting with a dose of 5 μg/kg/min, and increasing the dose at 5-minute intervals to 10, 20, 30, and 40 μg/kg/min. At the end of each stage, and at the conclusion of the test, clinical signs are recorded, and 2-dimensional images recorded and digitized. During the infusion, a 12-lead electrocardiogram is monitored continuously and recorded at 5-minute intervals. Blood pressure is measured with a sphygmomanometer at 5-minute intervals. Test end points are achievement of peak dose, attainment of 85% maximal predicted heart rate, development of ischemia (manifest as severe angina, ST-segment depression >2 mm, or a new or worsened abnormality in systolic wall motion or wall thickening) or the occurrence of severe side effects (systolic pressure >220 mm IIg, diastolic pressure >120 mm, >30 mm Hg decrease in systolic pressure, dyspnea, significant ventricular or supraventricular arrhythmia, or severe nausea/vomiting).

Studies may be performed with a Hewlett-Packard Sonos 2500 ultrasound system (Boston, Mass.) and recorded on half-inch VHS tape. Images are also digitized at the end of each test stage (rest and dobutamine doses) from 4 view (parastemal long- and short-axis views and apical 4- and 2-chamber views) using a commercial stress program.

The nondigitized images recorded on videotape and the digitized images stored on disk are independently interpreted by 2 investigators who have no knowledge of the trial phase. The left ventricle is divided into 16 segments. For each segment, systolic and wall motion and thickening are visually graded with a semi quantitative 4-grade scoring system (normal or hyperkinesia, 1; hypokinesia, 2; akinesia, 3; dyskinesia, 4). A wall motion score index is derived for the entire left ventricle using the sum of individual scores divided by the total number of analyzed segments. A test result is considered positive for myocardial ischemia when the wall motion score increased by >1 grade at peak stress. However, akinesia becoming dyskinesia is not considered a criterion for positivity, since this can be due to passive stretching rather than to "active" ischemia. In positive tests, the dobutamine infusion time (minutes) is also determined as the time interval from the beginning of drug infusion to the occurrence of the stress-induced asynergy. Peak dobutamine achieved dose is also evaluated.

For the interpretation of changes in resting ventricular function, cine loops from each view of 2 resting studies (baseline of DET on placebo and baseline of DET on TMZ) are generated for each patient. These are displayed in a quad-screen format and interpreted by 2 investigators blinded to therapeutic information.

Example 4

Protocol for Determining the Effect of Acute Thiazolidinedione Treatment on Ischemic Myocardial Dysfunction in Humans The efficacy of candidate insulin sensitizers in the disclosed methods is readily demonstrated in patients sustaining an acute ischemic event, such as unstable angina or acute myocardial ischemia or infarction. At initial presentation to hospital with such an event, patients are randomly and blindly assigned to placebo or insulin sensitizer treatment. Just prior to the first dose of placebo or insulin sensitizer, an assessment of left ventricular systolic and diastolic function is made by 2-dimensional and Doppler echocardiography. Echocardiographic studies are then repeated serially (every two days) during the hospitalization to determine temporal changes in systolic and diastolic left ventricular function. At 5–7 days following the acute ischemic event (or sooner if clinically indicated) patients undergo cardiac catheterization with placement of a thermodilution catheter in the anterior interventricular vein (for ischemia/infarction attributed to the anterior descending coronary artery) or the inferior cardiac vein (for ischemia/infarction located in the inferior myocardium) or the coronary sinus (if selective coronary vein catheterization cannot be accomplished or the ischemia/infarct territory is uncertain). Paired arterial and coronary vein (sinus) blood specimens are obtained for measurement of oxygen, glucose, lactate, and free fatty acid content, along with a measurement of coronary vein (sinus) blood flow by thermodilution. Plasma insulin is also measured. Myocardial oxygen consumption or substrate uptake is calculated as the product of coronary blood flow and the coronary arteriovenous concentration difference. Efficacy of treatment in the group receiving insulin sensitizer is manifest by: a) systolic function: insulin sensitizer group demonstrates less depression of regional and global left ventricular function than placebo group on serial echocardiograms performed during the treatment period, as measured by such techniques as a standard regional wall motion scoring system and estimation of left ventricular ejection fraction by planimetry in multiple planes; b) diastolic function: insulin sensitizer group demonstrates less abnormality of diastolic function than placebo group on serial Doppler echocardiograms performed during the treatment period, as measured by such techniques as isovolumic relaxation period, standard criteria for the mitral inflow signal, and maximal rate of LV diastolic expansion; echocardiographic comparisons is made at 1 year comparing the groups to each other and both groups to their respective baseline studies. c) myocardial metabolism: at cardiac catheterization, insulin sensitizer group demonstrates greater uptake of lactate and lower uptake of free fatty acids compared to the placebo group; in addition, insulin-sensitizer group demonstrates lower plasma insulin and free fatty acid concentrations but normal blood glucose levels; d) lower mortality rate in insulin-sensitizer group than in placebo group.

Example 5

Protocol for Determining the Effect of Chronic Thiazolidinedione Treatment on Ischemic Myocardial Dysfunction in Humans The efficacy of candidate insulin sensitizers in the disclosed methods is readily demonstrated in patients susceptible and at high statistical risk for an acute myocardial ischemic event based on known coronary artery disease with recent myocardial infarction and/or unstable angina. At baseline, patients are subject to an echocardiogram (2-dimensional and Doppler) to determine global and regional systolic and diastolic left ventricular function. Patients are then be randomly and blindly assigned to treatment with an insulin sensitizer or placebo. Patients are followed for 1 year, during which time 20–25% would ordinarily be expected to sustain death, non-fatal recurrent myocardial infarction or recurrent unstable angina. At the end of 1 year, echocardiographic studies are repeated. Efficacy of chronic treatment with an insulin sensitizer is indicated by: a) reduced mortality among insulin-sensitizer group; b) fewer non-fatal reinfarctions and/or episodes of recurrent unstable angina in insulin-sensitizer group; c) less abnormality of left ventricular systolic function on echocardiography, as assessed by the criteria indicated in Example 4; d) less abnormality of left ventricular diastolic function on echocardiography, as assessed by the criteria indicated in Example 4. Echocardiographic comparisons are made at 1 year comparing the groups to each other and both groups to their respective baseline studies; e) metabolism: insulin-sensitizer group demonstrates lower plasma insulin and free fatty acid concentrations but normal blood glucose levels.

Example 6

Protocol for Determining the Effect of Chronic Thiazolidinedione Treatment on Hypertension in Humans The efficacy of candidate insulin sensitizers in the disclosed methods as anti-hypertensive agents is readily demonstrated in patients with hypertension. For example, the efficacy of Compounds 1–12 in enhancing insulin sensitivity to supra normal levels and reducing hypertension in patients with normal insulin sensitivity (both healthy patients and patients with medically controlled insulin sensitivity) is demonstrated in the following testing protocol. Hypertensive patients are classified in one of three categories based on plasma insulin and glucose levels during metabolic testing: diabetic, pre-diabetic (impaired insulin sensitivity without overt diabetes), or non-diabetic (with normal baseline insulin sensitivity). Arterial hypertension will be defined by JNC-VI criteria. Patients in each category are randomly and blindly assigned to insulin sensitizer or placebo in a 16-week crossover design study (i.e., each patient is treated with insulin sensitizer for 8 weeks and placebo for 8 weeks, in random and blinded sequence). Blood pressure is measured by a health professional on 3 separate occasions during each of the following 3 weeks: the week prior to treatment, the $8^{th}$ week of treatment (prior to crossover) and the $16^{th}$ week of treatment (after crossover). In addition, ambulatory blood pressure monitoring is employed for 48 hours during each of these three weeks. Efficacy of insulin-sensitizers in treating hypertension in each category of patient (diabetic, pre-diabetic, or non-diabetic) is indicated by lower blood pressure (systolic and/or diastolic) during the period of treatment with the insulin sensitizing agent, compared with the placebo treatment period.

REFERENCES

1. Eberli FR, et al. *Circ Res* 1991;68:466–481.
2. Cross HR, et al. *Circ Res* 1996;78:282–291.
3. Lopaschuk GD, et al. *Circulation* 1997;95:313–315.
4. Liu B, et al. *Circ Res* 1996;79:940–8.
5. Renstrom B, et al. *Am J Physiol* 1990;259:H317–H323.
6. Wisneski JA, et al. *J Clin Invest* 1987;79:359–366.
7. Kurien V, et al. *Lancet* 1969;2:185–187.
8. Oliver MF, et al. *Lancet* 1994;343:155–158.
9. Randle PJ. *Circ Res* 1976;38(Suppl I):I-8–I-15.
10. Apstein CS, et al. *Circulation* 1997;96:1074–77.
11. Apstein CS, et al. *Circ Res* 1983;52:515–526.
12. Zhu P, Lu L, Xu Y, Greyson CR, Ursell PC, Schwartz GG. Glucose-insulin-potassium treatment improves recovery of systolic and diastolic ventricular function after regional low-flow ischemia in pigs. *Circulation*, 1999, in revision.
13. Fath-Ordoubadi F, et al. *Circulation* 1997;96:1152–1156.
14. Lewandowski ED, et al. *Circulation* 1995;91:2071–2079.
15. Stacpoole PW. *Metabolism* 1989;38:1124–44.
16. McCormack JG, et al. *Circulation* 1996;93:135–142.
17. Cocco G, et al. *Cardiovasc Pharmacol* 1992;20:131–8.
18. Libersa C, et al. *Cardiovasc Drugs Ther* 1990;4:808–9.
19. Detry JM, et al. *Br J Clin Pharmacol* 1994;37:279–288.
20. Black SC, et al. *J Cardiovasc Pharmacol* 1994;24:921–928.
21. Vedrinne C, et al. *J Cardiovasc Pharmacol* 1996;28:500–506.
22. Broderick TL, et al. *Circulation* 1993;87:972–981.
23. Iliceto S, et al. *J Am Coll Cardiol* 1995;26:380–387.
24. Sassen LM, et al. *Mol Cell Biochem* 1992;116:147–153.
25. Molaparast-Saless F, et al. *J Mol Cell Cardiol* 1987;19:509–520.
26. Renstrom B, et al. *Am J Physiol* 1990;259:H317–H323.
27. Jodalen H, et al. *J Mol Cell Cardiol* 1988;20:277–282.
28. Bachmann E, et al. *Pharmacology* 1988;36:238–248.
29. Sparano N, et al. *Pharmacotherapy* 1998;18:539–548.
30. Sreenan S, et al. *Am J Physiol* 1996;271:E742–7.
31. Kumar S; et al. *Diabetologia* 1996;39:701–9.
32. Inoue I et al., *Biochem Biophys Res Comm* 1997;235:113–6.
33. Bolli R. *Prog Cardiovasc Dis* 1998;40:477–516.
34. Nakamura Y, et al. *Br J Pharmacol* 1998;123:675–682.
35. Przyklenk K; Kloner RA. *J Cardiovasc Pharmacol* 1991; 18(Suppl 10):S93–101.
36. Bähr M, et al. *Diabetologia* 1996;39:766–774.
37. Martin G, et al. *J Biol Chem* 1997;272:28210–28217.
38. Shimabukuro M, et al. *Metabolism* 1996;45:1168–1173.
39. Schwartz GG, Xu Y, Greyson C, Cohen J, Lu L. *Cardiovasc Res* 1996; 32:1024–1037.
40. Schwartz GG, et al. *Am J Physiol* 1994;266:H521–H530.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. At present, the experimental evidence seems to us to suggest that the activity inhibiting or preventing myocardial ischemia arises from the mode of action of the insulin sensitizers, and so the chemical structure of the compounds is believed to be of less importance than their activities. Accordingly, any compound having insulin sensitizing activity may be used in the present invention.

What is claimed is:

1. A method for providing enhanced resistance to myocardial ischemia associated dysfunction comprising the step of administering to a human determined to be susceptible to myocardial ischemia an effective amount of an insulin sensitizer sufficient to enhance the resistance of the human to myocardial ischemia associated dysfunction.

2. The method of claim 1, wherein said insulin sensitizer is selected from the group consisting of thiazolidinedione compounds, oxazolidinedione compounds, isoxazolidinedione compounds and oxadiazolidinedione compounds.

3. The method of claim 1, wherein said insulin sensitizer is selected from the group consisting of thiazolidinedione compounds and isoxazolidinedione compounds.

4. The method of claim 1, wherein said insulin sensitizer is selected from the group consisting of compounds of formula (I):

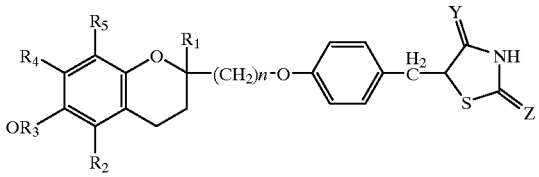

wherein:
$R^1$ and $R^2$ are the same as or different from each other and each represents a hydrogen atom or an alkyl group having from 1 to 5 carbon atoms;

$R^3$ represents a hydrogen atom, an aliphatic acyl group having from 1 to 6 carbon atoms, a cycloalkanecarbonyl group having from 5 to 7 carbon atoms in the cycloalkane part, a benzoyl group, a naphthoyl group, a benzoyl or naphthoyl group which is substituted by at least one substituent selected from the group consisting of substituents α, defined below, a heterocyclic acyl group in which the heterocyclic part has from 4 to 7 ring atoms of which from 1 to 3 are hetero-atoms selected from the group consisting of nitrogen, oxygen and sulfur atoms, a phenylacetyl group, a phenylpropionyl group, a phenylacetyl or phenylpropionyl group which is substituted by at least one halogen substituent, a cinnamoyl group, an alkoxycarbonyl group having from 1 to 6 carbon atoms in the alkoxy part or a benzyloxycarbonyl group;

$R^4$ and $R^5$ are the same as or different from each other and each represents a hydrogen atom, an alkyl group having from 1 to 5 carbon atoms or an alkoxy group having from 1 to 5 carbon atoms, or $R^4$ and $R^5$ together represent an alkylenedioxy group having from 1 to 4 carbon atoms;

n is 1, 2 or 3;

Y and Z are the same as or different from each other and each represents an oxygen atom or an imino group; and substituents a are selected from the group consisting of alkyl groups having from 1 to 4 carbon atoms, alkoxy groups having from 1 to 4 carbon atoms, halogen atoms, hydroxy groups, amino groups, alkylamino groups having from 1 to 4 carbon atoms, dialkylamino groups having from 1 to 4 carbon atoms in each alkyl part, and nitro groups;

and pharmaceutically acceptable salts thereof.

5. The method of claim 4, wherein said insulin sensitizer is selected from the group consisting of compounds of formula (Ia):

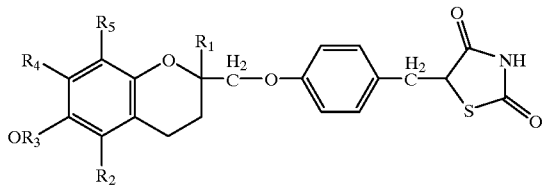

wherein:
$R^1$, $R^2$, $R^4$ and $R^5$ are the same as or different from each other and each represents a hydrogen atom or an alkyl group having from 1 to 5 carbon atoms; and $R^3$ represents a hydrogen atom, an aliphatic acyl group having from 1 to 6 carbon atoms, a benzoyl group, a naphthoyl group, a benzoyl or naphthoyl group which is substituted by at least one substituent selected from the group consisting of substituents α, defined below, or an alkoxycarbonyl group having from 1 to 6 carbon atoms in the alkoxy part;

substituents α are selected from the group consisting of alkyl groups having from 1 to 4 carbon atoms, alkoxy groups having from 1 to 4 carbon atoms, halogen atoms, hydroxy groups, amino groups, alkylamino groups having from 1 to 4 carbon atoms, dialkylamino groups having from 1 to 4 carbon atoms in each alkyl part, and nitro groups;

and pharmaceutically acceptable salts thereof.

6. The method of claim 4, wherein $R^1$ represents an alkyl group having from 1 to 4 carbon atoms.

7. The method of claim 4, wherein $R^2$ represents a hydrogen atom or an alkyl group having from 1 to 3 carbon atoms.

8. The method of claim 4, wherein $R^3$ represents a hydrogen atom, an aliphatic acyl group having from 1 to 4 carbon atoms, an unsubstituted benzoyl or naphthoyl group, or an alkoxycarbonyl group having from 2 to 4 carbon atoms.

9. The method of claim 4, wherein $R^4$ represents an alkyl group having from 1 to 4 carbon atoms.

10. The method of claim 4, wherein $R^5$ represents a hydrogen atom or an alkyl group having from 1 to 3 carbon atoms.

11. The method of claim 4, wherein:
$R^1$ represents an alkyl group having from 1 to 4 carbon atoms;
$R^2$ represents a hydrogen atom or an alkyl group having from 1 to 3 carbon atoms;
$R^3$ represents a hydrogen atom, an aliphatic acyl group having from 1 to 4 carbon atoms, an unsubstituted benzoyl or naphthoyl group, or an alkoxycarbonyl group having from 2 to 4 carbon atoms;
$R^4$ represents an alkyl group having from 1 to 4 carbon atoms; and
$R^5$ represents a hydrogen atom or an alkyl group having from 1 to 3 carbon atoms.

12. The method of claim 4, wherein $R^3$ represents a hydrogen atom, an acetyl group, a benzoyl group or an ethoxycarbonyl group.

13. The method of claim 4, wherein:
$R^1$ represents an alkyl group having from 1 to 4 carbon atoms;
$R^2$ represents a hydrogen atom or an alkyl group having from 1 to 3 carbon atoms;
$R^3$ represents a hydrogen atom, an acetyl group, a benzoyl group or an ethoxycarbonyl group;
$R^4$ represents an alkyl group having from 1 to 4 carbon atoms; and
$R^5$ represents a hydrogen atom or an alkyl group having from 1 to 3 carbon atoms.

14. The method of claim 4, wherein $R^1$ represents a methyl group.

15. The method of claim 4, wherein $R^2$ represents a hydrogen atom or a methyl group.

16. The method of claim 4, wherein $R^3$ represents a hydrogen atom, an acetyl group or an ethoxycarbonyl group.

17. The method of claim 4, wherein $R^4$ represents a methyl or a t-butyl group.

18. The method of claim 4, wherein $R^5$ represents a hydrogen atom or a methyl group.

19. The method of claim 4, wherein:

$R^1$ represents a methyl group;

$R^2$ represents a hydrogen atom or a methyl group;

$R^3$ represents a hydrogen atom, an acetyl group or an ethoxycarbonyl group;

$R^4$ represents a methyl or a t-butyl group; and $R^5$ represents a hydrogen atom or a methyl group.

20. The method of claim 5, wherein $R^1$ represents an alkyl group having from 1 to 4 carbon atoms.

21. The method of claim 5, wherein $R^2$ represents a hydrogen atom or an alkyl group having from 1 to 3 carbon atoms.

22. The method of claim 5, wherein $R^3$ represents a hydrogen atom, an aliphatic acyl group having from 1 to 4 carbon atoms, an unsubstituted benzoyl or naphthoyl group, or an alkoxycarbonyl group having from 2 to 4 carbon atoms.

23. The method of claim 5, wherein $R^4$ represents an alkyl group having from 1 to 4 carbon atoms.

24. The method of claim 5, wherein $R^5$ represents a hydrogen atom or an alkyl group having from 1 to 3 carbon atoms.

25. The method of claim 5, wherein:

$R^1$ represents an alkyl group having from 1 to 4 carbon atoms;

$R^2$ represents a hydrogen atom or an alkyl group having from 1 to 3 carbon atoms;

$R^3$ represents a hydrogen atom, an aliphatic acyl group having from 1 to 4 carbon atoms, an unsubstituted benzoyl or naphthoyl group, or an alkoxycarbonyl group having from 2 to 4 carbon atoms;

$R^4$ represents an alkyl group having from 1 to 4 carbon atoms; and $R^5$ represents a hydrogen atom or an alkyl group having from 1 to 3 carbon atoms.

26. The method of claim 5, wherein $R^3$ represents a hydrogen atom, an acetyl group, a benzoyl group or an ethoxycarbonyl group.

27. The method of claim 5, wherein:

$R^1$ represents an alkyl group having from 1 to 4 carbon atoms;

$R^2$ represents a hydrogen atom or an alkyl group having from 1 to 3 carbon atoms;

$R^3$ represents a hydrogen atom, an acetyl group, a benzoyl group or an ethoxycarbonyl group;

$R^4$ represents an alkyl group having from 1 to 4 carbon atoms; and $R^5$ represents a hydrogen atom or an alkyl group having from 1 to 3 carbon atoms.

28. The method of claim 5, wherein $R^1$ represents a methyl group.

29. The method of claim 5, wherein $R^2$ represents a hydrogen atom or a methyl group.

30. The method of claim 5, wherein $R^3$ represents a hydrogen atom, an acetyl group or an ethoxycarbonyl group.

31. The method of claim 5, wherein $R^4$ represents a methyl or a t-butyl group.

32. The method of claim 5, wherein $R^5$ represents a hydrogen atom or a methyl group.

33. The method of claim 5, wherein:

$R^1$ represents a methyl group;

$R^2$ represents a hydrogen atom or a methyl group;

$R^3$ represents a hydrogen atom, an acetyl group or an ethoxycarbonyl group;

$R^4$ represents a methyl or a t-butyl group; and $R^5$ represents a hydrogen atom or a methyl group.

34. The method of claim 1, wherein said insulin sensitizer is selected from the group consisting of: 5-[4-(6-hydroxy-2,5,7,8-tetramethylchroman-2-ylmethoxy)-benzyl]thiazolidine-2,4-dione and pharmaceutically acceptable salts thereof;

5-[4-(6-hydroxy-2-methyl-7-t-butylchroman-2-ylmethoxy)-benzyl]thiazolidine-2,4-dione and pharmaceutically acceptable salts thereof 5-[4-(6-hydroxy-2-ethyl-5,7,8-trimethylchroman-2-ylmethoxy)benzyl]thiazolidine-2,4-dione and pharmaceutically acceptable salts thereof;

5-[4-(6-hydroxy-2-isobutyl-5,7,8-trimethylchroman-2-ylmethoxy)benzyl]thiazolidine-2,4-dione and pharmaceutically acceptable salts thereof;

5-[4-(6-acetoxy-2,5,7,8-tetramethylchroman-2-ylmethoxy)benzyl]thiazolidine-2,4-dione and pharmaceutically acceptable salts thereof;

5-[4-(6-ethoxycarbonyloxy-2,5,7,8-tetramethylchroman-2-ylmethoxy)benzyl]thiazolidine-2,4-dione and pharmaceutically acceptable salts thereof;

5-[6-(2-fluorobenzyloxy)-2-naphthylmethyl] thiazolidine-2,4-dione and pharmaceutically acceptable salts thereof;

5-{4-[2-(5-ethylpyridin-2-yl)ethoxy]benzyl}thiazolidine-2,4-dione and pharmaceutically acceptable salts thereof;

5-(2-benzyl-3,4-dihydro-2H-benzopyran-6-ylmethyl)-thiazolidine-2,4-dione and pharmaceutically acceptable salts thereof;

5-[4-{2-[N-methyl-N-(pyridin-2-yl)amino]ethoxy}benzyl]-thiazolidine-2,4-dione and pharmaceutically acceptable salts thereof;

5-(4-{2-[1-(4-2'-pyridylphenyl)ethylideneaminooxy]ethoxy}-benzyl)thiazolidine-2,4-dione and pharmaceutically acceptable salts thereof;

4-{4-[2-(5-methyl-2-phenyloxazol-4-yl)ethoxy]benzyl}-isoxazolidine-3,5-dione and pharmaceutically acceptable salts thereof;

5-{4-(5-methoxy-3-methylimidazo[4,5-b]pyridin-2-ylmethoxy)benzyl}thiazolidine-2,4-dione and pharmaceutically acceptable salts thereof;

5-{4-(5-methoxy-3-methylimidazo[4,5-b]pyridin-2-ylmethoxy)benzyl}thiazolidine-2,4-dione and its hydrochloride;

5-[4-(6-methoxy-1-methylbenzimidazol-2-ylmethoxy)benzyl]thiazolidine-2,4-dione and pharmaceutically acceptable salts thereof;

5-[4-(1-methylbenzimidazol-2-ylmethoxy)benzyl]thiazolidine-2,4-dione and pharmaceutically acceptable salts thereof;

5-[4-(5-hydroxy-1,4,6,7-tetramethylbenzimidazol-2-ylmethoxy)benzyl]thiazolidine-2,4-dione and pharmaceutically acceptable salts thereof;

5-[4-(1-methylindolin-2-ylmethoxy)benzyl]thiazolidine-2,4-dione and pharmaceutically acceptable salts thereof; and 5-{4-[3-(5-methyl-2-phenyloxazol-4-yl)propionyl]benzyl}thiazolidine-2,4-dione and pharmaceutically acceptable salts thereof.

35. A method for reducing hypertension comprising the step of administering to a human determined to (a) be hypersensitive and (b) have normal baseline insulin sensitivity, an effective amount of an insulin sensitizer sufficient to reduce the hypertension of said human.

* * * * *

UNITED STATES PATENT AND TRADEMARK OFFICE
CERTIFICATE OF CORRECTION

PATENT NO.  : 5,968,960
DATED       : October 19, 1999
INVENTOR(S) : Gregory G. Schwartz Page 1 of 1

It is certified that error appears in the above-identified patent and that said Letters Patent is hereby corrected as shown below:

Column 1,
Line 9, after "Health", please insert -- , grant number HL499944 --.

Signed and Sealed this

Twenty-fifth Day of March, 2003

JAMES E. ROGAN
*Director of the United States Patent and Trademark Office*